(12) United States Patent
Adelsheim et al.

(10) Patent No.: US 11,724,126 B2
(45) Date of Patent: Aug. 15, 2023

(54) METHODS AND SYSTEMS FOR QUALITY-AWARE CONTINUOUS LEARNING FOR RADIOTHERAPY TREATMENT PLANNING

(71) Applicant: VARIAN MEDICAL SYSTEMS, INC., Palo Alto, CA (US)

(72) Inventors: Charles Adelsheim, Mountain View, CA (US); Corey Zankowski, Palo Alto, CA (US); Petr Jordan, Emerald Hills, CA (US)

(73) Assignee: VARIAN MEDICAL SYSTEMS, INC., Palo Alto, CA (US)

(*) Notice: Subject to any disclaimer, the term of this patent is extended or adjusted under 35 U.S.C. 154(b) by 948 days.

(21) Appl. No.: 16/447,980

(22) Filed: Jun. 21, 2019

(65) Prior Publication Data

US 2020/0398079 A1 Dec. 24, 2020

(51) Int. Cl.
*A61N 5/10* (2006.01)
*G06N 20/00* (2019.01)
(Continued)

(52) U.S. Cl.
CPC .......... *A61N 5/103* (2013.01); *A61N 5/1031* (2013.01); *A61N 5/1039* (2013.01);
(Continued)

(58) Field of Classification Search
CPC .......... A61N 2005/1041; A61N 5/103; A61N 5/1031; A61N 5/1039; A61N 5/1075
See application file for complete search history.

(56) References Cited

U.S. PATENT DOCUMENTS

2016/0140300 A1* 5/2016 Purdie .................. G16H 10/60
705/2
2019/0074079 A1 3/2019 Zankowski et al.
(Continued)

FOREIGN PATENT DOCUMENTS

WO 2015044924 A1 4/2015
WO 2018187598 A1 10/2018

OTHER PUBLICATIONS

International Search Report and Written Opinion of the International Searching Authority, International application No. PCT/US2020/037996, dated Sep. 21, 2020.
(Continued)

*Primary Examiner* — Christine H Matthews
(74) *Attorney, Agent, or Firm* — Su IP Consulting

(57) ABSTRACT

Example methods and systems for quality-aware continuous learning for radiotherapy treatment planning are provided. One example method may comprise: obtaining an artificial intelligence (AI) engine that is trained to perform a radiotherapy treatment planning task. The method may also comprise: based on input data associated with a patient, performing the radiotherapy treatment planning task using the AI engine to generate output data associated with the patient; and obtaining modified output data that includes one or more modifications made by a treatment planner to the output data. The method may further comprise: performing quality evaluation based on (a) first quality indicator data associated with the modified output data, and/or (b) second quality indicator data associated with the treatment planner. In response to a decision to accept, a modified AI engine may be generated by re-training the AI engine based on the modified output data.

24 Claims, 11 Drawing Sheets

(51) Int. Cl.
  *G06N 7/01* (2023.01)
  *G06V 10/778* (2022.01)

(52) U.S. Cl.
  CPC ......... *A61N 5/1075* (2013.01); *A61N 5/1081* (2013.01); *G06N 7/01* (2023.01); *G06N 20/00* (2019.01); *G06V 10/7784* (2022.01)

(56) References Cited

U.S. PATENT DOCUMENTS

2020/0129780 A1* 4/2020 Lachaine ............... G16H 30/20
2020/0360731 A1* 11/2020 Tilly ...................... G16H 50/20

OTHER PUBLICATIONS

Simon K. Warfield et al., "Simultaneous Truth and Performance Level Estimation (STAPLE): An Algorithm for the Validation of Image Segmentation", IEEE Transactions on Medical Imaging, Jul. 2004, vol. 23, Issue 7.

* cited by examiner

METHODS AND SYSTEMS FOR QUALITY-AWARE CONTINUOUS LEARNING FOR RADIOTHERAPY TREATMENT PLANNING

BACKGROUND

Unless otherwise indicated herein, the approaches described in this section are not prior art to the claims in this application and are not admitted to be prior art by inclusion in this section.

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, to achieve this goal, conventional radiotherapy treatment planning may be time and labor intensive.

SUMMARY

According to examples of the present disclosure, methods and systems for quality-aware continuous learning for radiotherapy treatment planning are provided. In this case, one example method may comprise: obtaining an artificial intelligence (AI) engine that is trained to perform a radiotherapy treatment planning task. The method may also comprise: based on input data associated with a patient, performing the radiotherapy treatment planning task using the AI engine to generate output data associated with the patient; and obtaining modified output data that includes one or more modifications made by a treatment planner to the output data.

The example method may further comprise: performing quality evaluation based on (a) first quality indicator data associated with the modified output data, and/or (b) second quality indicator data associated with the treatment planner. In response to a decision to accept, a modified AI engine may be generated by re-training the AI engine based on the modified output data.

DETAILED DESCRIPTION

The technical details set forth in the following description enable a person skilled in the art to implement one or more embodiments of the present disclosure.

Figure 1:
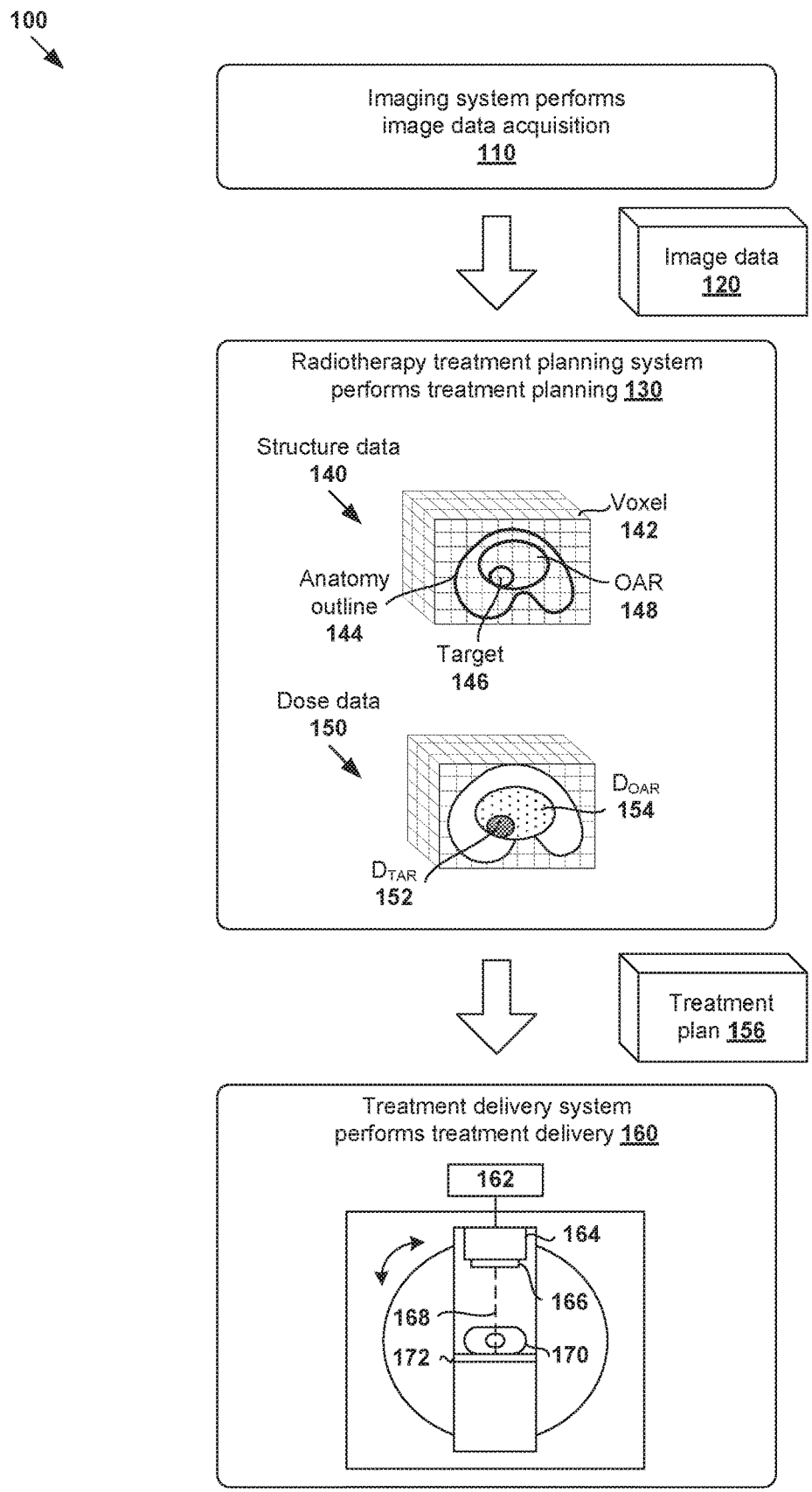
FIG. 1 is a schematic diagram illustrating an example process flow for radiotherapy treatment.

FIG. 1 is a schematic diagram illustrating example process flow 100 for radiotherapy treatment. Example process 100 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or 4D CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures from image data 120. In practice, a three-dimensional (3D) volume of the patient's anatomy may be reconstructed from image data 120. The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may be include any suitable data relating to the contour, shape, size and location of patient's anatomy 144, target 146, organ-at-risk (OAR) 148, etc. In practice, OAR 148 may represent any suitable delineated organ, non-target structure (e.g., bone, tissue, etc.), etc.

For example, using image segmentation, a line may be drawn around a section of an image and labelled as target 146 (e.g., tagged with label="prostate"). Everything inside the line would be deemed as target 146, while everything outside would not. In another example, dose prediction may be performed to generate dose data 150 specifying radiation dose to be delivered to target 146 (denoted "$D_{TAR}$" at 152) and radiation dose for OAR 148 (denoted "$D_{OAR}$" at 154). In practice, target 146 may represent a malignant tumor (e.g., prostate tumor, etc.) requiring radiotherapy treatment, and OAR 148 a proximal healthy structure or non-target structure (e.g., rectum, bladder, etc.) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated to include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system, etc. In practice, block 130 may be performed based on goal doses prescribed by a clinician (e.g., oncologist, dosimetrist, planner, etc.), such as based on the clinician's experience, the type and extent of the tumor, patient geometry and condition, etc.

At 160 in FIG. 1, treatment delivery is performed during a treatment phase to deliver radiation to the patient according to treatment plan 156. For example, radiotherapy treatment delivery system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156. The radiation may be designed to be curative, palliative, adjuvant, etc.

It should be understood that any suitable radiotherapy treatment delivery system(s) may be used, such as mechanic-arm-based systems, tomotherapy type systems, brachytherapy, SIR-spheres, radiopharmaceuticals, any combination thereof, etc. Additionally, examples of the present disclosure may be applicable to particle delivery systems (e.g., proton, carbon ion, etc.). Such systems may employ either a scattered particle beam that is then shaped by a device akin to an MLC, or a scanning beam of adjustable energy, spot size and dwell time.

Conventionally, radiotherapy treatment planning at block 130 in FIG. 1 is time and labor intensive. For example, it usually requires a team of highly skilled and trained oncologists and dosimetrists to manually delineate structures of interest by drawing contours or segmentations on image data 120. These structures are manually reviewed by a physician, possibly requiring adjustment or re-drawing. In many cases, the segmentation of critical organs can be the most time-consuming part of radiation treatment planning. After the structures are agreed upon, there are additional labor-intensive steps to process the structures to generate a clinically-optimal treatment plan specifying treatment delivery data such as beam orientations and trajectories, as well as corresponding 2D fluence maps.

Further, treatment planning is often complicated by a lack of consensus among different physicians and/or clinical regions as to what constitutes "good" contours or segmentation. In practice, there might be a huge variation in the way structures or segments are drawn by different clinical experts. The variation may result in uncertainty in target volume size and shape, as well as the exact proximity, size and shape of OARs that should receive minimal radiation dose. Even for a particular expert, there might be variation in the way segments are drawn on different days. Due to the lack of consistency, treatment planning might result in different clinical outcomes for patients and it is difficult to evaluate whether a final treatment plan is "good."

According to examples of the present disclosure, artificial intelligence (AI) techniques may be applied to ameliorate various challenges associated with radiotherapy treatment planning. Throughout the present disclosure, the term "AI engine" may refer generally to any suitable hardware and/or software component(s) of a computer system capable of executing algorithms according to any suitable AI model(s), such as deep learning model(s), etc. The term "deep learning" may refer generally to a class of approaches that utilizes many layers or stages of nonlinear data processing for feature learning as well as pattern analysis and/or classification. The "deep learning model" may refer to a hierarchy of "layers" of nonlinear data processing that include an input layer, an output layer, and multiple (i.e., two or more) "hidden" layers between the input and output layers. These layers may be trained from end-to-end (e.g., from the input layer to the output layer) to extract feature(s) from an input and classify the feature(s) to produce an output (e.g., classification label or class). The term "deep learning engine" may refer to any suitable hardware and/or software component(s) of a computer system capable of executing algorithms according to any suitable deep learning model(s).

Depending on the desired implementation, any suitable AI model(s) may be used, such as convolutional neural network, recurrent neural network, deep belief network, or any combination thereof, etc. In practice, a neural network is generally formed using a network of processing elements (called "neurons," "nodes," etc.) that are interconnected via connections (called "synapses," "weights," etc.). For example, convolutional neural networks may be implemented using any suitable architecture(s), such as U-net, LeNet, AlexNet, ResNet, V-net, DenseNet, etc. In this case, a "layer" of a convolutional neural network may be a convolutional layer, pooling layer, rectified linear units (ReLU) layer, fully connected layer, loss layer, etc. In practice, the U-net architecture includes a contracting path (left side) and an expansive path (right side). The contracting path includes repeated application of convolutions, followed by a ReLU layer and max pooling layer. Each step in the expansive path may include upsampling of the feature map followed by convolutions, etc.

Deep learning approaches should be contrasted against machine learning approaches that have been applied to, for example, automatic segmentation. In general, these approaches involve extracting (hand-designed) feature vectors from images, such as for every voxel, etc. Then, the feature vectors may be used as input to a machine learning model that classifies which class each voxel belongs to. However, such machine learning approaches usually rely on a high dimension of hand-designed features in order to accurately predict the class label for each voxel. Solving a high-dimensional classification problem is computationally expensive and requires a large amount of memory. Some approaches use lower dimensional features (e.g., using dimensionality reduction techniques) but they may decrease the prediction accuracy.

Conventionally, there are many challenges associated with training AI engines (e.g., deep learning engines) for radiotherapy treatment planning. For example, different planners generally have different clinical practices in radiotherapy treatment planning. To train an AI engine according to a specific clinical practice, one option is to develop a specific in-house model. However, it may be difficult to achieve desirable training results without collecting a huge amount of carefully-curated training data. Also, while conceptually simple, training AI engines generally requires significant technical expertise relating to model architecture(s), optimization, convergence analysis, regularization, etc. These challenges may lead to suboptimal results or, worse, failure to create any working AI engines. Such complexity may deter users from training and using AI engines for radiotherapy treatment planning, which is undesirable.

Quality-Aware Continuous Learning

According to examples of the present disclosure, quality-aware continuous learning may be implemented to improve the performance of AI engines for radiotherapy treatment planning. As used herein, the term "continuous learning" (also known as "lifelong learning," "incremental learning" and "sequential learning") may refer generally to technique(s) where an AI engine is modified or improved throughout its operation based on additional training data. The term "quality-aware" may refer generally to a quality evaluation process for deciding whether continuous learning should be performed.

Using a quality-aware approach, a trained AI engine may be modified or improved over time based on training data that has been evaluated. By improving the quality and adaptability of AI engines, treatment planning outcome may also be improved for patients, such as increasing the tumor control probability and/or reducing the likelihood of health complications or death due to radiation overdose in the healthy structures, etc. Examples of the present disclosure may be deployed in any suitable manner, such as a stand-alone computer system, web-based planning-as-a-service (PaaS) system, or any combination thereof, etc.

Figure 2:
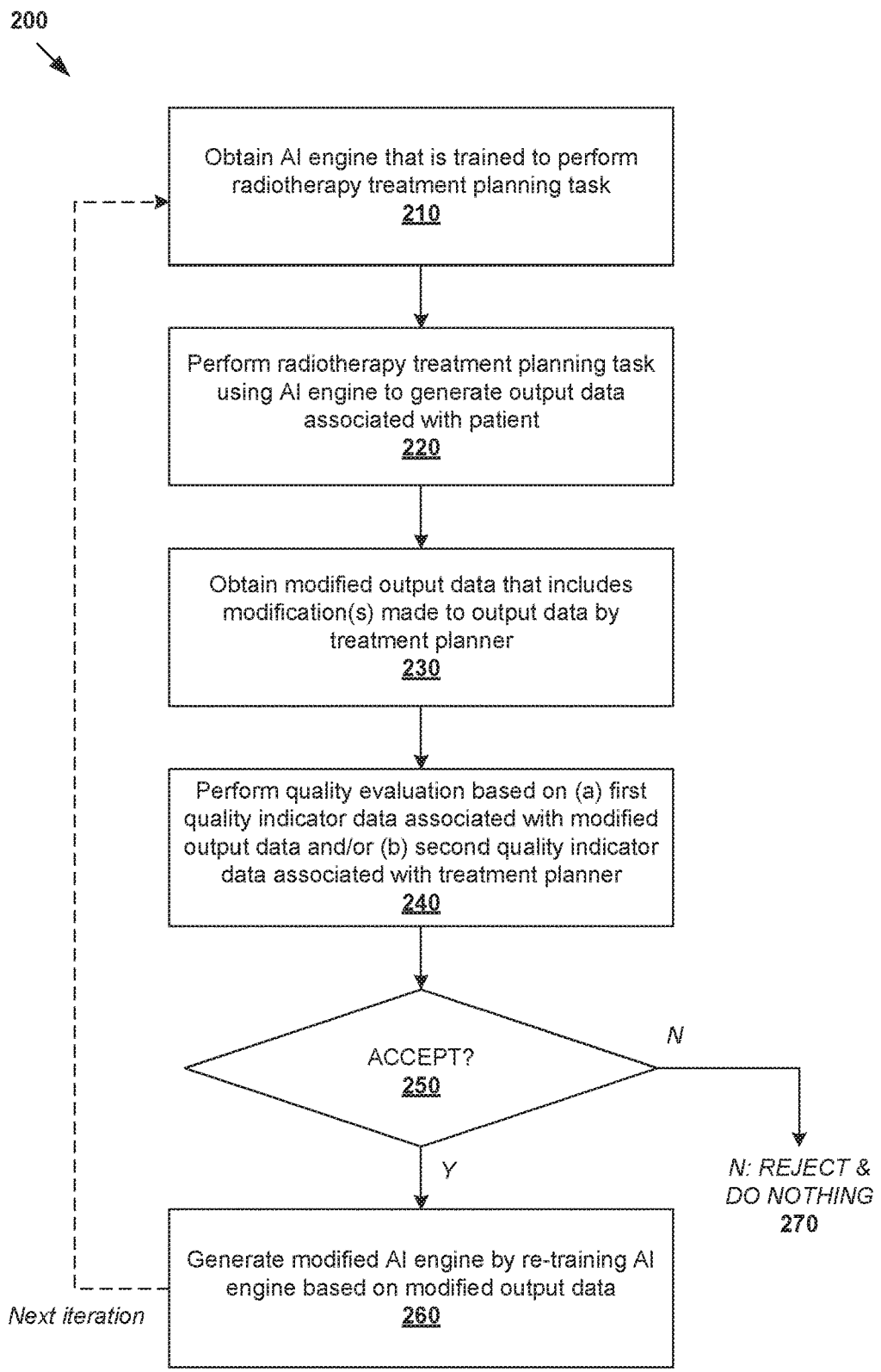
FIG. 2 is a flowchart of an example process for a computer system to perform quality-aware continuous learning for radiotherapy treatment planning.

In more detail, FIG. 2 is a flowchart illustrating example process 200 for a computer system to perform quality-aware continuous learning for radiotherapy treatment planning. Example process 200 may include one or more operations, functions, or actions illustrated by one or more blocks, such as 210 to 270. The various blocks may be combined into fewer blocks, divided into additional blocks, and/or eliminated based upon the desired implementation. Example process 200 may be implemented using any suitable computer system(s), an example of which will be discussed using FIG. 11. Some examples will be explained using FIG. 3, which is a schematic diagram illustrating example quality-aware continuous learning for radiotherapy treatment planning according to the example in FIG. 2.

At 210 in FIG. 2, a treatment planning AI engine (see 320 in FIG. 3) that is trained to perform a radiotherapy treatment planning task may be obtained. Here, the term "obtain" may refer generally to a computer system accessing, or retrieving data and/or computer-readable instructions associated with, AI engine 320 from any suitable source (e.g., another computer system), memory or datastore (e.g., local or remote), etc. AI engine 320 may be trained during training phase 301 based on first training data (see 310 in FIG. 3) that includes treatment plans associated with multiple past patients. Note that "first training data" 310 may include synthetic training data, which are training cases derived from past patients.

At 220 in FIG. 2, AI engine 320 may be used to perform the radiotherapy treatment planning task during inference phase 302. For example, based on input data (see 330 in FIG. 3) associated with a particular patient, AI engine 320 may perform the radiotherapy treatment planning task to generate output data (see 340 in FIG. 3) associated with the patient. In practice, AI engine 320 may be trained to perform any suitable radiotherapy treatment planning task, such as automatic segmentation, dose prediction, treatment delivery data estimation, abnormal organ detection, treatment outcome prediction, or any combination thereof.

In the case of automatic segmentation, AI engine 320 may be trained to generate output=structure data (e.g., 140 in FIG. 1) based on input=image data (e.g., 120 in FIG. 1). In the case of dose prediction, engine 320 may be trained to generate output=dose data (e.g., 150 in FIG. 1) based on input=structure data and beam geometry data. In the case of treatment delivery data estimation, engine 320 may be trained to generate output=treatment delivery data (e.g., fluence map data, structure projection data, etc.) based on input=structure data and/or dose data, etc.

At 230 in FIG. 2, modified output data (see 350 in FIG. 3) that includes modification(s) to output data 340 may be obtained. The term "modification" may refer generally to an addition, deletion, correction, change, movement, selection or alteration that may be made to output data. Modified output data 350 may be generated by a treatment planner (see 355 in FIG. 3). Here, a "treatment planner" or "planner" may refer generally to an individual, a group of individuals, an institution, a clinical site or network, a clinical region, or any combination thereof. For example, an individual may be a dosimetrist, clinician, physicist, medical personnel, etc. In some situations, a "treatment planner" may be another computerized algorithm.

In practice, the modification(s) may be made by a treatment planner 355 according to any suitable clinical guideline(s), planning strategy and/or planning practice(s) associated with the treatment planner. For example, in the case of automatic segmentation (to be discussed using FIG. 4), modified output data 350 may include a modification made to segmentation margins associated with a structure (e.g., OAR or target). In relation dose prediction (to be discussed using FIG. 7), modified output data 350 may include a modification made to OAR sparing, etc. Any alternative and/or additional modification(s) may be used.

At 240 in FIG. 2, quality evaluation of modified output data 350 may be performed based on (a) first quality indicator data (see 360/361 in FIG. 3) associated with modified output data 350 and/or (b) second quality indicator data (see 360/362 in FIG. 3) associated with treatment planner 355. As used herein, the term "quality indicator data" may refer generally to any qualitative and/or quantitative factor(s) or variable(s) that help inform a decision process as to whether to perform continuous learning based on modified output data 350.

Figure 3:
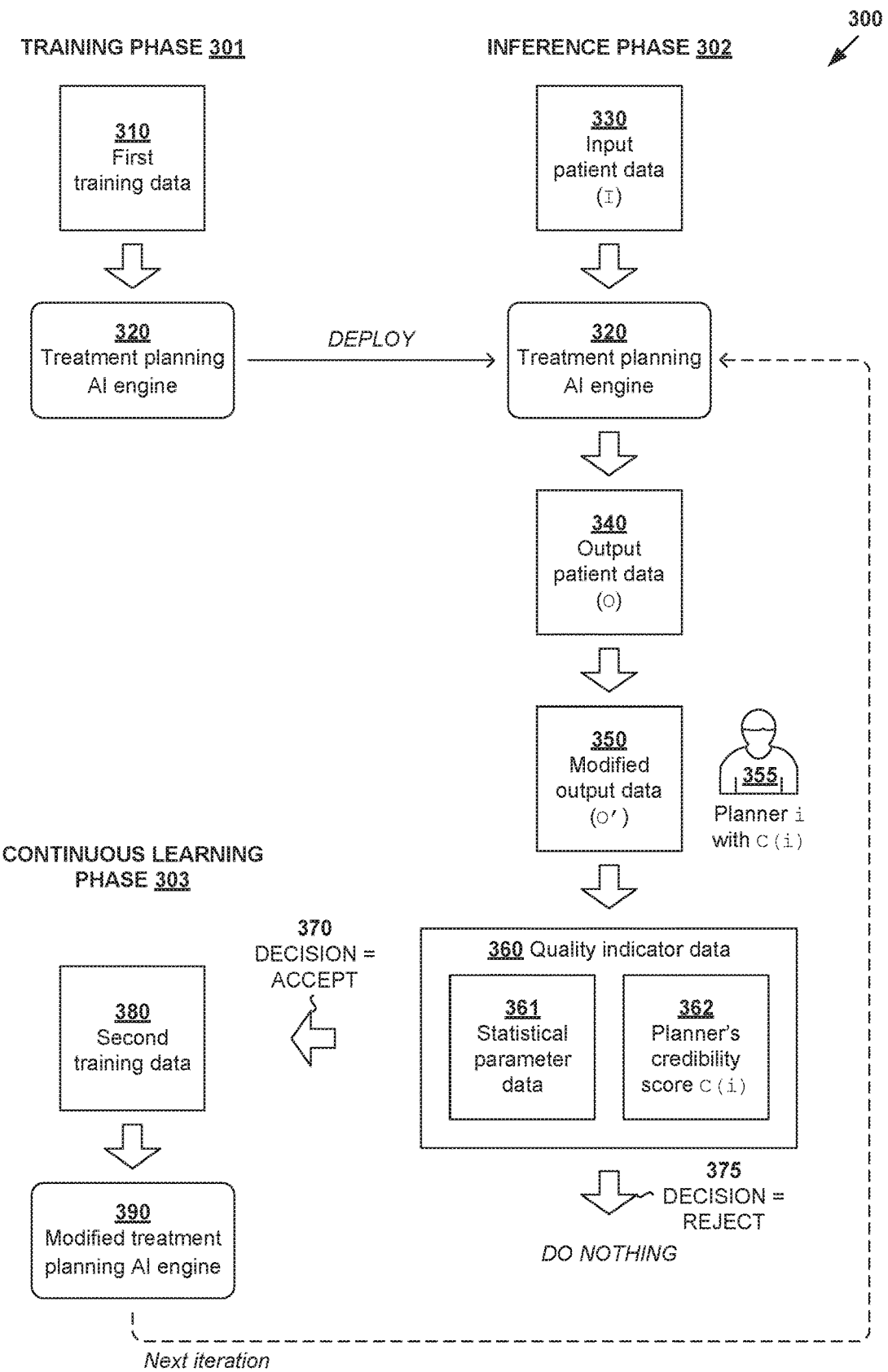
FIG. 3 is a schematic diagram illustrating example quality-aware continuous learning for radiotherapy treatment planning according to the example in FIG. 2.

In the example in FIG. 3, block 240 may include determining first quality indicator data in the form of statistical model parameter data (see 361 in FIG. 3) by applying statistical model(s) on modified output data 350. Additionally and/or alternatively, block 240 may include identifying the $i^{th}$ treatment planner from multiple planners, and determining second quality indicator data in the form of a credibility score C(i) assigned to the $i^{th}$ treatment planner (see 362 in FIG. 3). The term "credibility score" (to be discussed further using FIG. 6) may refer generally to any suitable quantitative measure that represents a reputation or trustworthiness of a particular treatment planner.

At 250 in FIG. 2, a decision may be made as to whether to accept modified output data 350 for continuous learning based on the quality evaluation at block 240. At 260 in FIG. 2, in response to a decision to accept (see 370 in FIG. 3), modified AI engine (see 390 in FIG. 3) may be generated by re-training AI engine 320 based on modified output data 360 during continuous learning phase 303. Otherwise, at 270 in FIG. 2, continuous learning based on modified output data 360 will not be performed (see also 375 in FIG. 3). In practice, the re-training process at block 260 may involve modifying or improving weight data associated with AI engine 320. Further, block 260 may involve generating second training data (see 380 in FIG. 3) based on modified output data 360 for the re-training process. A case weight may also be assigned to modified output data 360 based on (a) first quality indicator data 361 and/or (b) second quality indicator data 362 to influence the re-training process.

Depending on the desired implementation, the re-training process at block 260 may be performed for a batch of modified output data 350. For example, the batch may include modification(s) made by multiple treatment planners over a period of time. For quality assurance purposes, the re-training process may be performed periodically so that re-trained or modified AI engine 350 may undergo some form of quality assurance checks prior to deployment.

According to examples of the present disclosure, continuous learning phase 303 may be improved using additional training data that has been evaluated for quality. If rejected, continuous learning will not be performed, thereby improving efficiency and reducing the negative impact of inferior or redundant training data. Various examples will be discussed below using FIG. 4 to FIG. 11. In particular, an example automatic segmentation will be discussed using FIG. 4, an example quality evaluation using FIG. 5, an example credibility score assignment using FIG. 6, an example dose prediction using FIG. 7, an example multi-technique AI engine using FIG. 8, various use cases for credibility scores using FIG. 9, an example treatment plan using FIG. 10, and an example computer system using FIG. 11.

Automatic Segmentation Example

Figure 4:
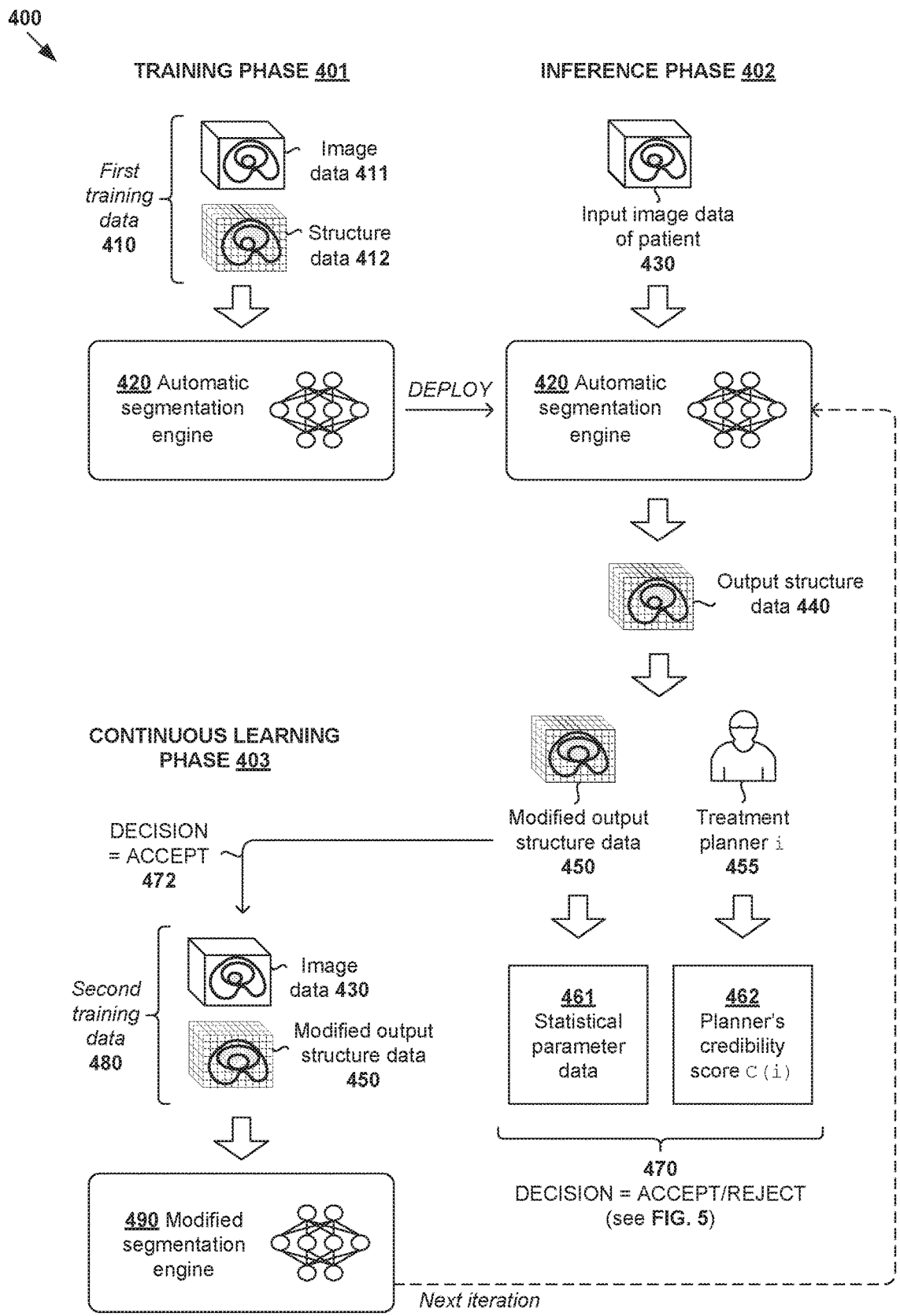
FIG. 4 is a schematic diagram illustrating example quality-aware continuous learning for automatic segmentation.

FIG. 4 is a schematic diagram illustrating example quality-aware continuous learning for automatic segmentation 400. In this example, AI engine 420 (also referred to as "segmentation engine" below) may be trained using first training data 410 during training phase 401; applied to perform automatic segmentation during inference phase 402; and updated during continuous learning phase 403. In practice, the output of automatic segmentation may be used for abnormal organ detection, dose prediction, treatment delivery data estimation, etc.

(a) Training Phase (See 401 in FIG. 4)

During training phase 401, segmentation engine 420 may be trained to map training image data 411 (i.e., input) to training structure data 412 (i.e., output). In practice, image data 411 may include 2D or 3D images of a patient's anatomy, and captured using any suitable imaging modality or modalities. Structure data 412 may identify any suitable contour, shape, size and/or location of structure(s) from image data 411. Example structures may include target(s), OAR(s) or any other structure of interest (e.g., tissue, bone) of the anatomical site. Depending on the desired implementation, structure data 412 may identify multiple targets and OARs of any suitable shapes and sizes.

For example, in relation to prostate cancer, image data 411 may include images of site=prostate region. In this case, structure data 412 may identify a target representing each patient's prostate, and OARs representing proximal healthy structures such as rectum and bladder. In relation to lung cancer treatment, image data 411 may include images of a lung region. In this case, structure data 412 may identify a target representing cancerous lung tissue, and an OAR representing proximal healthy lung tissue, esophagus, heart, etc. In relation to brain cancer, image data 411 may include images of a brain region. Structure data 412 may identify a target representing a brain tumor, and an OAR representing a proximal optic nerve, brain stem, etc.

First training data 410 may be extracted or derived from past treatment plans developed for multiple past patients according to any desirable planning rule. First training data 410 may be pre-processed using any suitable data augmentation approach (e.g., rotation, flipping, translation, scaling, noise addition, cropping, any combination thereof, etc.) to produce a new dataset with modified properties to improve model generalization using ground truth. In practice, a 3D volume of the patient that will be subjected to radiation is known as a treatment volume, which may be divided into multiple smaller volume-pixels (voxels). In this case, structure data 412 may specify a class label (e.g., "target," "OAR," etc.) associated with each voxel in the 3D volume.

In one example in FIG. 4, segmentation engine 420 includes multiple (N>1) processing blocks or layers that are each associated with a set of weight data. In this case, training phase 401 may involve finding weight data that minimizes a training error between training structure data 412, and estimated structure data (not shown for simplicity) generated by segmentation engine 420. The training process is guided by estimating losses associated with the classification error. A simple example of a loss function would be mean squared error between true and predicted outcome, but the loss function could have more complex formulas. This loss can be estimated from the output of the model, or from any discrete point within the model.

(b) Inference Phase (See 402 in FIG. 4)

At 430 and 440 in FIG. 4, trained segmentation engine 420 may be used to perform automatic segmentation for a particular patient during inference phase 402. Input image data 430 associated with that patient is processed using segmentation engine 420 to generate output structure data 440. For example, output structure data 440 may identify any suitable contour, shape, size and/or location of structure(s) in input image data 430.

At 450 in FIG. 4, output structure data 440 may be modified by the treatment planner 455 to achieve a preferred segmentation outcome. For example, modified output structure data 450 may include modification(s) made by planner 455 to the contour, edges, shape, size and/or location of structure(s) in output structure data 440. In the case of automatic segmentation, a modification may refer to moving, adjusting or redrawing segmentation(s). For example, modified output structure data 450 may include different segmentation margin(s), identify an additional and/or alternative structure, etc.

(c) Continuous Learning Phase (See 403 in FIG. 4)

At 461-462 and 470 in FIG. 4, a quality evaluation may be performed based on any suitable quality indicator data to decide whether to accept modified output data 450 for continuous learning. As will be discussed further using FIG. 5, the quality evaluation may be based on statistical parameter data 461 ("first quality indicator data") that is generated by identifying and applying statistical model(s) on modified output data 450. Alternatively and/or additionally, credibility score 462 ("second quality indicator data") associated with treatment planner 455 may be obtained.

In one example, the quality evaluation may involve performing a first filtering of modified output data 450 based on statistical parameter data 461. If a first threshold is satisfied (and credibility score 462 is available), a second filtering is then performed based on credibility score 462. In this case, statistical parameter data 461 may be used to determine whether modification(s) made by treatment planner 455 provide any measurable improvement according to the statistical model(s). When combined with credibility score 462 associated with treatment planner 455 that made the modification, modified output data 450 may be categorized to be "high value" (i.e., decision=ACCEPT) or "low value" (i.e., decision=REJECT). Some examples will be discussed below using FIG. 5.

At 480 and 490 in FIG. 4, in response to a decision to accept (see 472) modified output data 450 for continuous learning based on the quality evaluation, segmentation engine 420 may be updated based on second training data 480. In practice, second training data 480 may include example input-output pair in the form of image data 430 processed by segmentation engine 420, and modified output structure data 450 that includes modification(s) desired by planner 455. Once continuous learning is performed, modified segmentation engine 480 may be deployed for use in the next iteration of inference phase 402. If modification is made to subsequent output structure data generated by modified engine 480, quality evaluation and continuous learning phase 403 may be repeated for further improvement.

Quality Evaluation

Figure 5:
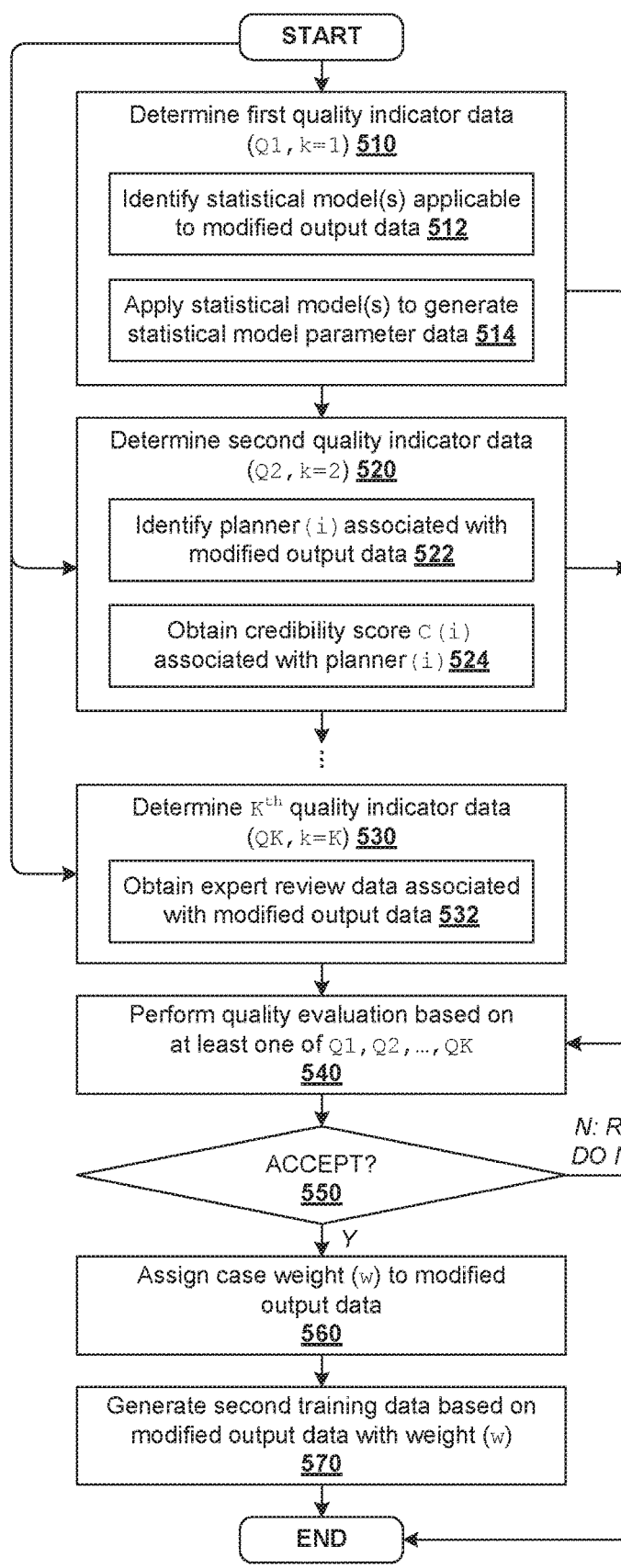
FIG. 5 is a flowchart of an example process for quality evaluation to facilitate quality-aware continuous learning for radiotherapy treatment planning.

FIG. 5 is a flowchart illustrating example process 500 for quality evaluation to facilitate quality-aware continuous learning for radiotherapy treatment planning. Example process 500 may include one or more operations, functions, or actions illustrated by one or more blocks, such as 510 to 570. The various blocks may be combined into fewer blocks, divided into additional blocks, and/or eliminated based upon the desired implementation. Example process 500 may be implemented using any suitable computer system(s), an example of which will be discussed using FIG. 11.

In practice, any suitable quality indicator data denoted as $Q_k$ (where $k=1, \ldots, K$) may be used for quality evaluation. As will be described further below, the quality indicator data may include statistical parameter data (see 510), credibility score (see 520), expert review data (see 530), etc. This way, at 540, quality evaluation of modified output data 450 may be performed based on any combination of quality indicator data ($Q_1, \ldots, Q_K$).

(a) Statistical Parameter Data

At 510 in FIG. 5, first quality indicator data (Q1 for k=1) in the form of statistical parameter data 461 may be determined. Block 510 may involve identifying and applying statistical model(s) to the modified output data 450. See 512-514 in FIG. 5. In practice, the term "statistical model" may refer generally to a model for evaluating a probability of certain measurable quantity (also known as an attribute, feature or parameter) derivable from modified output data 450. This way, statistical parameter data 461 may be used to indicate the reliability or validity of modified output data 450 associated with planner 455 in FIG. 4.

Any suitable "statistical model" may be used, ranging from simple metric(s) to more complex model(s). The statistical model may return a single value (i.e., scalar) or multiple values (vector). Further, the "probability" evaluated using a statistical model may be unconditional (e.g., describes the statistics of the quantity over the whole set of training data) or conditional (e.g., describes the statistics of some quantity in condition that certain previous intermediate result has been obtained). For example, structure size could be used unconditionally (e.g., it has the same criteria regardless of the CT scan), or it could be conditional to some values derived from the CT scan (e.g., total area of non-zero region in the slice going through the center of the given organ).

In the case of automatic segmentation in FIG. 4, statistical models may be applied to evaluate a probability of certain attribute associated with a patient's structure data 450, such as its shape, size, texture, contour, principal component analysis, material density, geometric distribution, or Hounsfield Units (HU) distribution, relative position of the structure to another structure, etc. For example, in relation to prostate cancer treatment, statistical parameter data 461 may be generated based on a statistical model for evaluating the sphericity of a prostate (i.e., target).

In the case of dose prediction, statistical models may be applied to evaluate certain attribute(s) associated with dose data, such as DVH, D20, D50, dose fall-off gradient, etc. Other statistical models may be used for evaluating treatment delivery data, such as smoothness of 2D fluence maps; total motion of leaves in VMAT plan, beam orientations, machine trajectories, any combination thereof, etc. Depending on the radiotherapy treatment planning task that an AI engine is trained to perform, any alternative and/or additional statistical model(s) that are known in the art may be used.

(b) Credibility Score

At 520 in FIG. 5, second quality indicator data (Q2 for k=2) in the form of credibility score 462 may be determined. Block 520 may involve identifying a particular $i^{th}$ planner 455 responsible for the modification(s) in modified output data 450, and obtaining a credibility score C(i) associated with the planner. See also 522-524 in FIG. 5. In practice, the $i^{th}$ planner may be identified from multiple (P>1) planners who are each assigned with credibility score C(i), where $i=1, \ldots, P$. Any suitable approach may be used for credibility score assignment. Some examples will be explained using FIG. 6, which is a schematic diagram illustrating example process 600 for credibility score assignment to facilitate quality-aware continuous learning for radiotherapy treatment planning.

At 610 and 620, multiple (N) treatment planning cases may be selected for a "planning contest" that involves multiple (P) treatment planners. At 630, each $i^{th}$ planner-generated output data D(i, j) for each $j^{th}$ case may be obtained, where $i=1, \ldots, P$ and $j=1, \ldots, N$. For example, D(1, 3) refers to a first planner's (i=1) output data for a third case (j=3), and D(4, N) to a fourth planner's (i=4) output data for the $N^{th}$ case (j=N). As previously noted, a "planner" may represent an individual, a group of individual, an institution, a clinical site or network, etc.

In practice, treatment planning cases 620 may be new cases specifically selected for the planning contest, or historical cases (e.g., from historical planning contests). These cases may be "sprinkled" into each planner's daily workflow. In both cases, examples of the present disclosure may provide a built-in procedure for cross-calibration and consensus truth analysis for multiple patients. A given case (j) may be used in such a calibration process until adding the output data of new planners fails to substantially affect its corresponding consensus truth G(j). The calibration process may be presented as a training program for planners (e.g., human delineators) to help develop and maintain their skills over time.

In a first example (see 640 in FIG. 6), credibility score C(i) may be assigned based on a comparison between planner-generated output data D(i, j) and consensus truth data associated with cases j=1, . . . , N. For the $j^{th}$ case, its consensus truth data may be denoted as G(j) and determined based on corresponding all planner-generated output data D(i, j) for that case, where i=1, . . . , P. In this case, G(j) may be an average or mean of output data D(i, j) for planners i=1, . . . , P. Using a normal distribution for D(i, j) as an example, the consensus truth data for the $j^{th}$ case may be determined using $G(j)=1/P \sum_{i=1}^{N} D(i, j)$. Any other distribution may be used. A smaller deviation will lead to a higher credibility score, and a higher deviation to a lower credibility score.

In practice, the term "ground truth" or "absolute truth" may refer generally to the "ideal" or "optimal" output data for the $j^{th}$ case. Since the "ground truth" may not exist, the "consensus truth" G(j) for the $j^{th}$ case may be determined from output data D(i, j) produced by multiple planners to represent the "gold standard." In this case, a credibility score may be assigned to a planner on the basis of their ability to consistently produce output data in accordance with the current consensus truth. As will be discussed further below, when multiple clusters of practice patterns are identified, the term "consensus truth" may refer to the mean or average of a particular cluster (cohort). For example, if there are M clusters, G(j, m) may represent the consensus truth of the $m^{th}$ cluster for the $j^{th}$ case, where m=1, . . . , M.

In a second example (see 650 in FIG. 6), credibility score C(i) may be assigned based on cluster analysis data 650 associated with D(i, j). Here, cluster analysis data 650 may identify multiple (M) clusters indicating different self-similar methodologies used by the planners. In practice, cluster analysis may be performed when D(i, j) for a particular $j^{th}$ case converges into separate clusters. In this case, the set of planners may be increased with additional planners (e.g., P+1, P+2, and so on). Output data D(i>P, j) generated by the additional planners may then be added until the clusters separates from each other "cleanly" based on any suitable threshold. In this case, the credibility score C(i) of the $i^{th}$ planner may be determined based on the deviation between the planner-generated output data D(i, j) and the consensus truth G(j, m) of a particular $m^{th}$ cluster. As practice patterns move over time (and the number of clusters changes), the continuous learning process may be led by the most credible planners who have higher case weights, or by masses of new practitioners who emerge as a new cluster.

In a third example (see 660 in FIG. 6), credibility score C(i) may be assigned based on expert review data 660 associated with a review of output data generated by each planner, such as by a panel of human experts. In a first approach, the panel may review D(i, j) for the planning contest in FIG. 6 and/or each planner's historical plans to evaluate their plan quality, segmentation accuracy, etc. In a second approach, each time a particular planner makes a substantial correction (e.g., adjusting a contour by more than 1-2 sigma in inter-observer variability from the result) using a treatment planning system, the correction may be automatically flagged in the system. The correction is then reviewed by a panel of individuals who are regarded as experts in their field. In this case, expert review data 660 may indicate the "value" of the correction or output data associated with each planner. Based on expert review data 660, the credibility score C(i) for the planner may be increased, or decreased.

In a fourth example (see 670 in FIG. 6), credibility score C(i) may be assigned based on algorithm comparison data 670 that evaluates a deviation between (i) planner-generated output data that includes D(i, j) and/or historical plans and (ii) algorithm-generated output data. For example, the selected algorithm may be designed to produce result that is close to the consensus truth. In this case, algorithm comparison data 670 may include parameter(s) that compare the planner- and algorithm-generated output data, such as similarity measure, mean deviation, self-consistency measure, etc. If the deviation is high, a lower credibility score will be assigned. Otherwise, a higher credibility score will be assigned.

To evaluate internal consistency for a particular planner, one approach is to calculate a mean deviation between the (i) planner-generated output data and (ii) the algorithm-generated output data over many cases, and the offset each planner's result by the mean deviation. The average deviation from the offset (over many cases) may be used as a measure of self-consistency. High self-consistency and a notable mean deviation (offset) from the algorithm indicate a behavioral bias or cluster. Another approach to evaluate internal consistency is to perform a clustering analysis of a planner's historical plans. For example, historical plans may be divided into multiple tranches based on any suitable factor(s), such as time (AM or PM), month, year, geographical location, etc. Multiple AI engines may be trained using training data associated with respective trances. Once trained, the AI engines may be used to process a set of test cases to evaluate whether they converge or diverge, such as based on a temporal factor, etc. A convergence would indicate high internal consistency, whereas a divergence would indicate low internal consistency.

Figure 6:
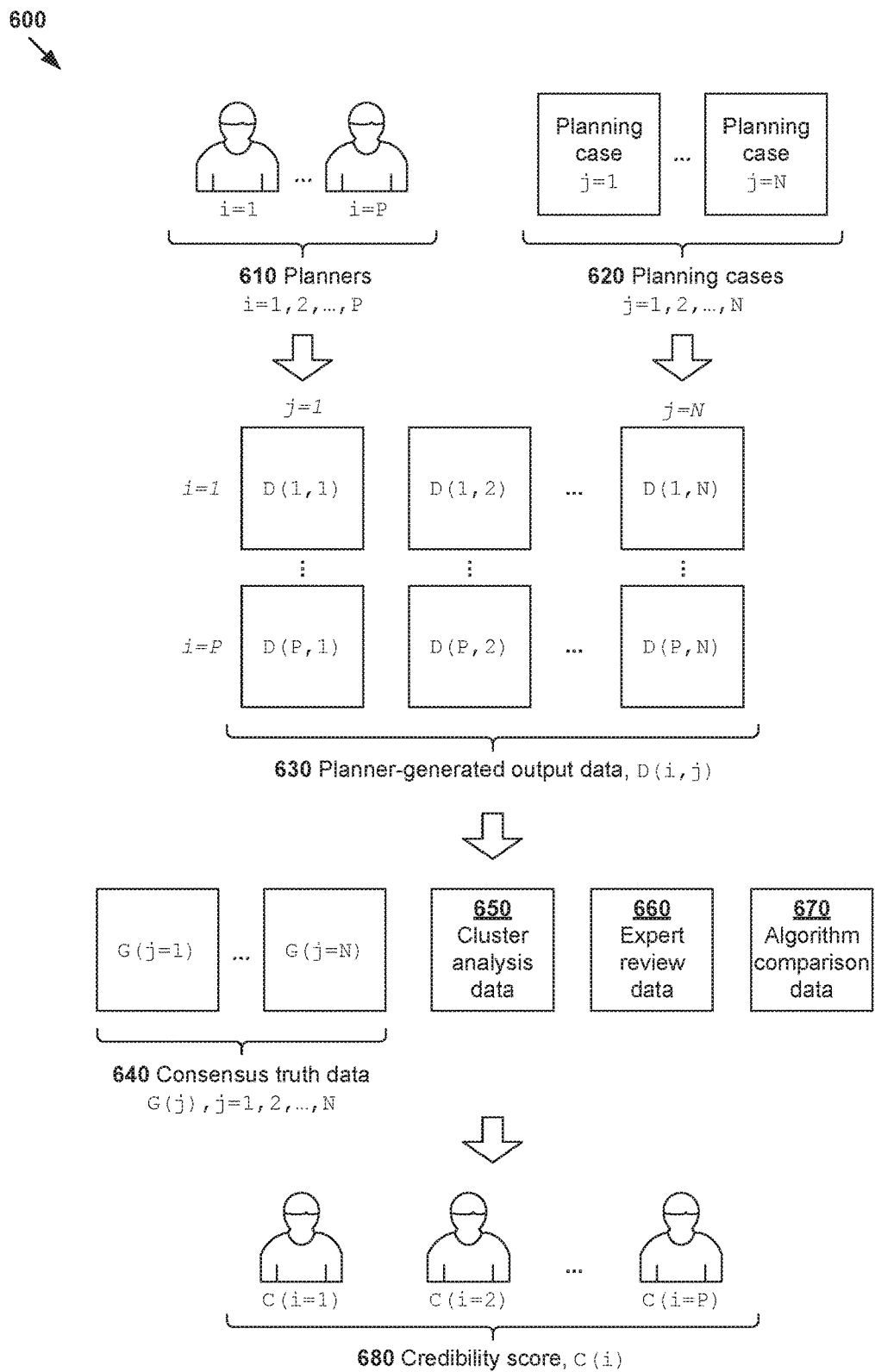
FIG. 6 is a schematic diagram illustrating an example process for credibility score assignment to facilitate quality-aware continuous learning for radiotherapy treatment planning.

At 680 in FIG. 6, a credibility score C(i) may be assigned to each $i^{th}$ planner based on any combination of the following: consensus truth data 640, cluster analysis data 650, expert review data 660, algorithm comparison data 670, etc. The examples in FIG. 6 may be repeated at any suitable frequency to update the credibility score assigned to each planner. Over time, good performers will have a higher credibility score compared to poor performers. Planners may be compared based on their respective credibility scores, such as how they stand in percentiles compared to others.

(c) Accept or Reject Decision

Referring to FIG. 5 again, at 530, any additional and/or alternative quality indicator data may be determined, such as expert review data associated with a review of modified output data 450 by a panel of human experts. This way, at 540, quality evaluation of modified output data 450 may be performed based on any combination of quality indicator data (Q1, . . . , QK) discussed above. For example, if the credibility score of a planner is lower than a particular threshold, the modification(s) made by the planner may be ignored during continuous learning for efficiency.

At 550, 560 and 570 in FIG. 5, in response to a decision to accept modified output data 450, second training data 480 may be generated to facilitate quality-aware continuous learning. Depending on the desired implementation, a case weight (w) may be assigned to modified output structure data 450 to influence the continuous learning process. For example, the case weight may be assigned based on the credibility score C(i) associated with the $i^{th}$ planner 455. A higher C(i) will lead to a higher case weight (w1) to indicate a relatively higher measure of reliability, whereas a lower C(i) will lead to a lower case weight (w2<w1) to reduce its influence in modified segmentation engine 480. Additionally and/or alternatively, the case weight (w) may be assigned based on statistical parameter data 461 associated with modified output structure data 450. See corresponding 560-570 in FIG. 5.

In another example, a case weight (w) may be a function of several factors, including magnitude of change δ (i) made by the $i^{th}$ planner 455, credibility score C(i) associated with the $i^{th}$ planner 455, etc. For a planner with a substantially low credibility score, a small change may be ignored. A big change may be reviewed a panel of human experts. If accepted by the panel, the change may be assigned with a low case weight (w) before being added to the new training set. For a more credible planner with a substantially high credibility score, a small change made by the planner may be accepted. A big change may be reviewed by the panel, and assigned with a higher case weight (w) if accepted. This way, changes made by a more credible planner will potentially have more material influence on modified AI engine 490. It should be understood that any suitable thresholds may be set to determine whether a planner's credibility score is "low" (e.g., $C(i) \leq C_{threshold}$) or "high" (e.g., $C(i) > C_{threshold}$), and whether the corresponding magnitude of change is "small" (e.g., $\delta(i) \leq \delta_{threshold}$) or "big" (e.g., $\delta(i) > \delta_{threshold}$).

Dose Prediction and Other Tasks

Figure 7:
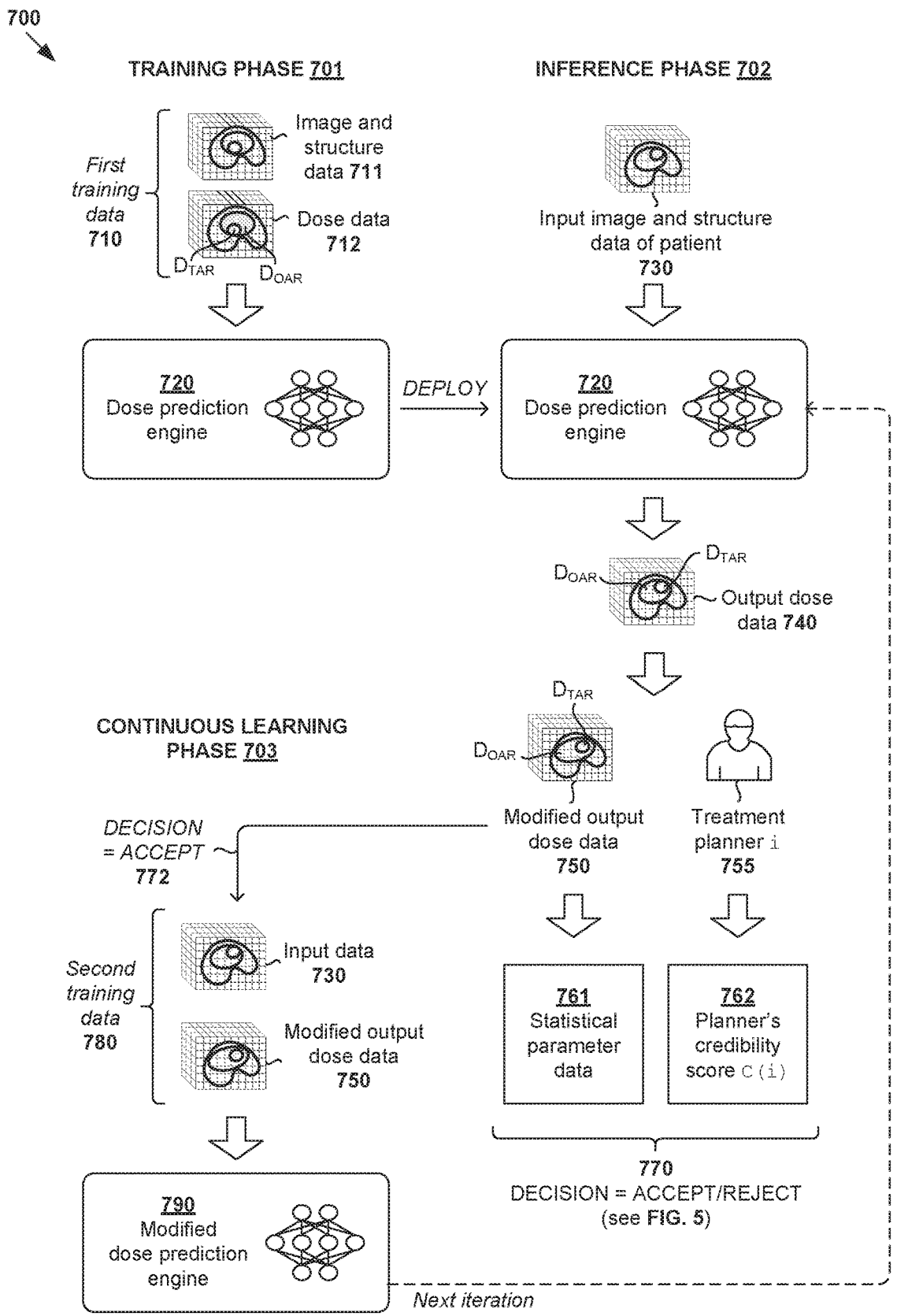
FIG. 7 is a schematic diagram illustrating example quality-aware continuous learning for dose prediction.

Examples of the present disclosure may be implemented for other treatment planning tasks. FIG. 7 is a schematic diagram illustrating example quality-aware continuous learning for dose prediction 700. In this example, dose prediction engine 720 may be trained using first training data 710 during training phase 701; applied to perform dose prediction during inference phase 702; and updated during continuous learning phase 703 based on quality evaluation.

During training phase (see 701 in FIG. 7), first training data 710 may be used to train dose prediction engine 720. First training data 710 may include image and structure data 711 (i.e., training input) and dose data 712 (i.e., training output) associated with multiple past patients. Dose data 712 (e.g., 3D dose data) may specify dose distributions for a target (denoted "$D_{TAR}$") and an OAR (denoted "$D_{OAR}$"). For example, in relation to prostate cancer, dose data 712 may specify dose distributions for a target representing the patient's prostate, and an OAR representing a proximal healthy structure such as rectum or bladder. In practice, dose data 712 may specify the dose distributions for the whole 3D volume, not just the target and OAR volumes. Dose data 712 may include spatial biological effect data (e.g., fractionation corrected dose) and/or cover only part of the treatment volume. Any additional input data may be used to train dose prediction engine 720, such as beam geometry data associated with the treatment delivery system.

During inference phase (see 702 in FIG. 7), dose prediction engine 720 may be used to generate output dose data 740 based on input image and structure data 730 associated with a particular patient. Dose data 740 may specify dose distributions for an OAR ("$D_{OAR}$") and a target ("$D_{TAR}$"). Modification(s) may then be made by treatment planner 755 (e.g., dosimetrist) to generate modified output dose data 750 based on any suitable dose prediction practice(s) preferred by the planner. The modification(s) may be associated with OAR sparing, target coverage, target dose prescription, normal tissue dose, location of dose gradients, steepness of dose gradients, orientation of dose gradients, etc.

During continuous learning phase (see 703 in FIG. 7), quality evaluation may be performed based on statistical parameter 761 and/or credibility score 762 associated with planner 755 responsible for the modification(s). As discussed using FIG. 5, example statistical models for evaluating certain attribute(s) associated with dose data 740/750 may be used, such as D20, D50, dose fall-off gradient, etc. Credibility score 762 may be generated according to the example in FIG. 6, in which case planner-generated dose data D(i, j) may be used.

In response to determination to accept modified output dose data 750 for continuous learning based on the quality evaluation (see 770-772 in FIG. 7), modified dose prediction engine 790 may be generated by re-training dose prediction engine 720 based on second training data 780. Similar to the example in FIG. 4, second training data 780 may include (input, output) pair in the form of input image and structure data 730 and modified output dose data 750. Once validated and approved, modified dose prediction engine 790 may be deployed for use in the next iteration of inference phase 702. If modification is made to output dose data generated by modified engine 780, continuous learning phase 703 may be repeated for further improvement.

Besides automatic segmentation in FIG. 4 and dose prediction in FIG. 7, quality-aware continuous learning may be implemented for other radiotherapy treatment planning tasks, such as treatment delivery data estimation, treatment outcome prediction, etc. The estimated treatment delivery data (i.e., output data) may include structure projection data, fluence map data, etc. For example, an AI engine may be trained to perform structure projection data, such as based on image data, structure data, dose data, or any combination thereof. Structure projection data may include data relating to beam orientations and machine trajectories for a treatment delivery system.

In another example, an AI engine may be trained to perform fluence map estimation, such as 2D fluence maps for a set of beam orientations or trajectories, machine control point data (e.g., jaw and leaf positions, gantry and couch positions), etc. Fluence maps will be explained further using FIG. 8. Any additional and/or alternative training data may be used, such as field geometry data, monitor units (amount of radiation counted by machine), quality of plan estimate (acceptable or not), daily dose prescription (output), field size or other machine parameters, couch positions parameters or isocenter position within patient, treatment strategy (use movement control mechanism or not, boost or no boost), treat or no treat decision, etc.

Multi-Technique AI Engines

Figure 8:
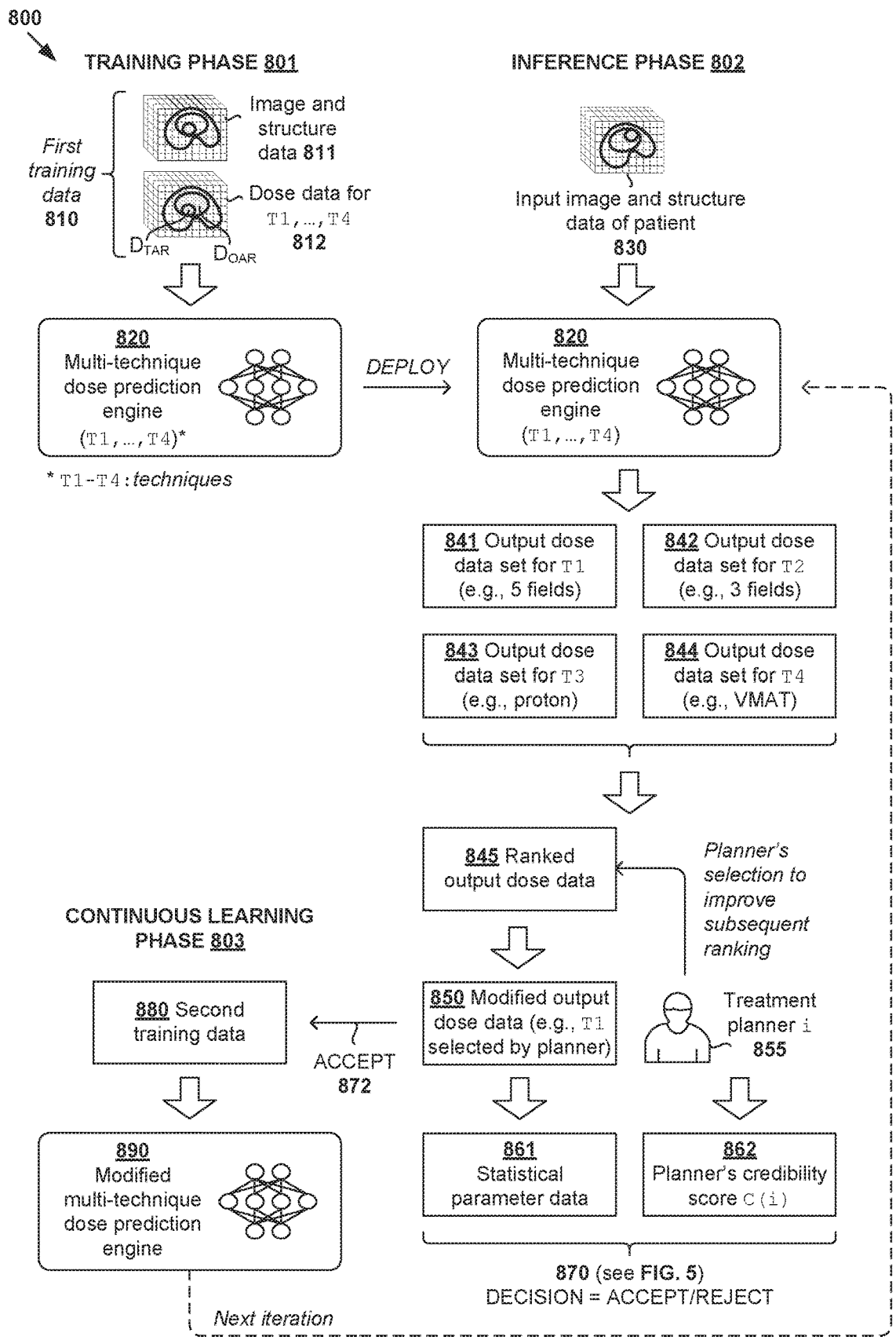
FIG. 8 is a schematic diagram illustrating example quality-aware continuous learning for radiotherapy treatment planning using a multi-technique AI engine.
Figure 9:
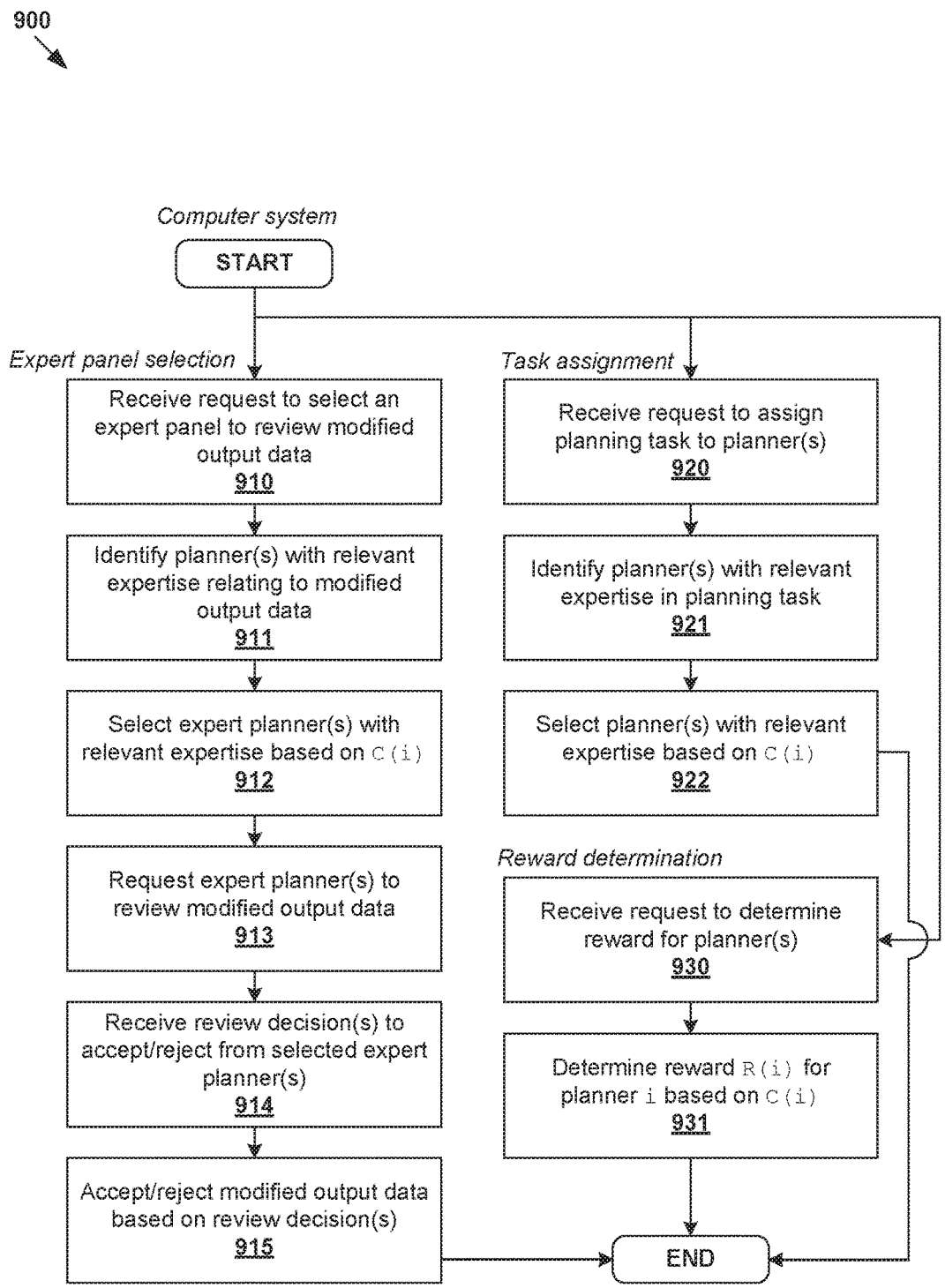
FIG. 9 is a flowchart of an example process for expert panel selection, planning task assignment and reward determination based on credibility score.

Examples of the present disclosure may be used to facilitate quality-aware continuous learning for multi-technique AI engines for radiotherapy treatment planning. FIG. 8 is a schematic diagram illustrating example quality-aware continuous learning 800 for radiotherapy treatment planning using a multi-technique AI engine. Similar to the example in FIG. 7, dose prediction engine 820 in FIG. 8 is a multi-technique AI engine that is trained to perform dose prediction using multiple techniques. Here, the term "multi-technique AI engine" may refer generally to a single AI engine, or a group of multiple AI engines that are trained according to respective techniques.

During training phase (see 801 in FIG. 8), first training data 810 may be used to train multi-technique dose prediction engine 820 to generate multiple sets of output data. First training data 810 may include image and structure data 811 (i.e., training input) and dose data 812 (i.e., training output) associated with multiple techniques denoted as (T1, T2, T3, T4). Example image data, structure data and dose data explained using FIGS. 4-7 are also applicable here and will not be repeated for brevity.

During inference phase (see 802 in FIG. 8), multi-technique dose prediction engine 820 may be used to generate multiple sets of output dose data 841-844 based on input image and structure data 830 associated with a particular patient. For each technique, dose data 840 may specify dose distributions for any suitable structures (e.g., OAR and target). For example, first set 841 may be generated based on a first technique (e.g., T1=5 fields) for treatment delivery, second set 842 based on a second technique (e.g., T2=3 fields), third set 843 based on a third technique (e.g., T3=proton therapy), and fourth set 844 based on a fourth technique (e.g., T4=VMAT). In practice, each set of output dose data may be evaluated based on any suitable factor(s) during inference phase 802, such as deliverability, adherence to dose prescription, collision, OAR limits, machine parameters, any combination thereof, etc.

In the example in FIG. 8, multiple sets 841-844 generated using different techniques (T1, T2, T3, T4) are then ranked using a cost function. In the case of dose prediction, the cost function may be based on time, complexity, DVH, any combination thereof, etc. In the case of segmentation, the cost function may be based on segmentation-related parameter(s), such as segmentation mean, etc. In practice, the cost function may be designed for a problem (representing a mathematical ground truth) in which an optimal solution may be found. This way, sets 841-844 may be processed using the cost function and ranked accordingly. Further, a generative adversarial network (GAN), or any other suitable generative model, may be set up to create new techniques to explore options for which no previously trained AI engine exists.

The ranked list (see 845) may then be presented to treatment planner 855 for selection. Any suitable metric(s) may be presented along with each technique to guide the selection process, such as the cost function metrics discussed above. Selection may then be made by treatment planner 855 (e.g., dosimetrist) to generate modified output dose data 850. For example, if the first technique is selected, first set 841 (i.e., based on T1=5 fields) may be used as modified output dose data 850. Treatment planner 855 may also make any additional modification(s) to first set 841. The planner's selection may be used to improve or update the approach used for ranking multiple sets of output data in the next iteration (see arrow from 855 to 845 in FIG. 8).

During continuous learning phase (see 803 in FIG. 8), quality evaluation may be performed based on statistical parameter 861 and/or credibility score 862 associated with planner 855. In response to a decision to accept modified output dose data 850 for continuous learning based on the quality evaluation (see 870-872 in FIG. 8), modified engine 890 may be generated by updating or re-training multi-technique engine 820 based on second training data 880. Similar to the example in FIG. 4, second training data 880 may include (input, output) pair in the form of input data 830 and modified output dose data 850 (e.g., first set 841). Once validated and approved, modified dose prediction engine 890 may be deployed for use in the next iteration of inference phase 802 to facilitate further improvement. Using the example in FIG. 8, multi-technique comparisons may be performed using AI engines, which generally improves efficiency compared to brute force techniques.

Other Use Cases of Credibility Score

According to examples of the present disclosure, a credibility score C(i) may be assigned to a planner to facilitate various aspects of quality-aware continuous learning. Some additional use cases will be discussed using FIG. 9, which is a flowchart of example process 900 for request processing based on credibility score. Example process 900 may include one or more operations, functions, or actions illustrated by one or more blocks, such as 910 to 931. The various blocks may be combined into fewer blocks, divided into additional blocks, and/or eliminated based upon the desired implementation. Example process 900 may be implemented using any suitable computer system(s), an example of which will be discussed using FIG. 11. The computer system may be configured to perform example process 900 according to a user's request to perform any one of the following: expert panel selection, planning task assignment, reward determination, etc. The user's request may be generated using any suitable user interface, such as application programming interface (API), graphical user interface (GUI), command line interface (CLI), etc.

In relation to expert panel selection (see 910-915 in FIG. 9), the computer system may be configured to select, from multiple treatment planners, a panel of "experts" to review modified output data (e.g., 350/450/750) based on their credibility score C(i). This way, an expert panel may be assembled periodically to perform quality evaluation by reviewing modification(s) made by other planners, and deciding whether to accept the modification(s). Depending on the credibility score, the expert panel may be updated over time to reflect changing practices.

In one example, in response to receiving a request for expert panel selection, a planner with the relevant expertise may be identified and selected based on their credibility score C(i). For example, a selected planner may be one whose quality metric seems to have been violated the most by the modification(s) in the modified output data. Each expert (i.e., selected planner) is then requested to review the modified output data, such as by sending the expert an anonymized snapshot of the modification(s). After performing an offline review, each expert may submit their individual decision (e.g., vote) as to whether to accept or reject. A final decision may be made based on review decisions submitted by different experts. If accepted, the modified output data will be used as part of training data for continuous learning purposes.

In relation to task assignment (see 920-922 in FIG. 9), certain planning tasks may be assigned to certain planners based on their credibility score. In this case, the computer system may be configured to select, from multiple planners, a particular planner to perform a particular planning task based on their credibility score C(i). In one example, in response to receiving a request for task assignment, planner(s) with relevant expertise relating to the planning task may be identified and selected. For example, a planning task relating to breast cancer might be assigned to a planner who has the highest credibility score and expertise relating to breast cancer treatment. Another planning task relating to prostate cancer might be assigned to a different planner who is most credible in prostate cancer treatment.

In relation to reward determination (see 930-931 in FIG. 9), a reward (e.g., monetary reward, promotion, award, etc.) may be determined for a planner based on their credibility score. For example, a reward R(i) for the $i^{th}$ planner may be proportional to the planner's C(i). A more credible planner should receive a better reward compared to a less credible planner. The reward may be used as an incentive for planners to improve their credibility score over time.

Example Treatment Plan

Figure 10:
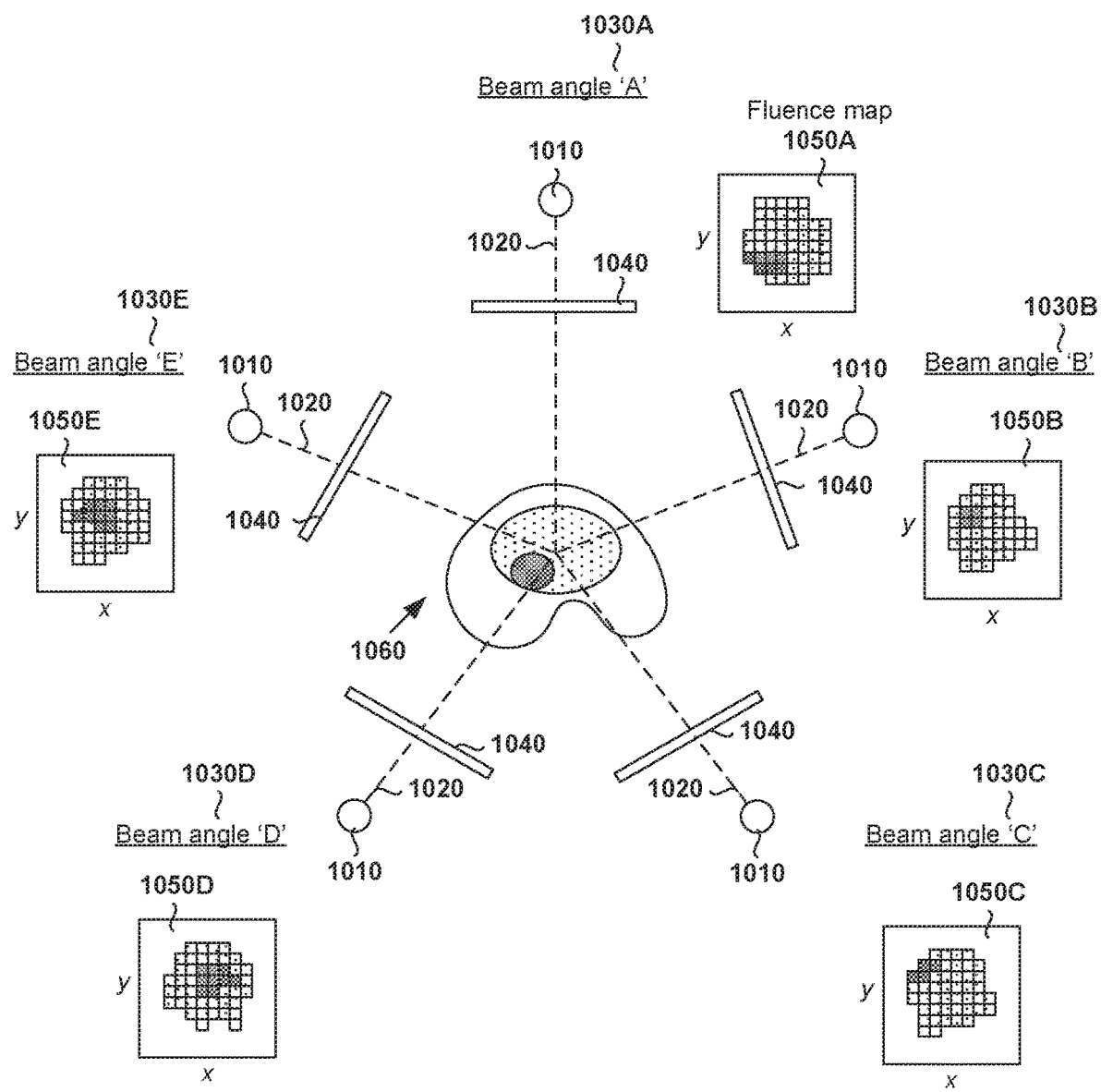
FIG. 10 is a schematic diagram of an example treatment plan for treatment delivery.

During radiotherapy treatment planning, treatment plan 156/1000 may be generated based on structure data and/or dose data generated using treatment planning engines discussed above. For example, FIG. 10 is a schematic diagram of example treatment plan 156/1000 generated or improved based on output data in the examples in FIG. 1 to FIG. 9. Treatment plan 156 may be delivered using any suitable treatment delivery system that includes radiation source 1010 to project radiation beam 1020 onto treatment volume 1060 representing the patient's anatomy at various beam angles 1030.

Although not shown in FIG. 10 for simplicity, radiation source 1010 may include a linear accelerator to accelerate radiation beam 1020 and a collimator (e.g., MLC) to modify or modulate radiation beam 1020. In another example, radiation beam 1020 may be modulated by scanning it across a target patient in a specific pattern with various energies and dwell times (e.g., as in proton therapy). A controller (e.g., computer system) may be used to control the operation of radiation source 1020 according to treatment plan 156.

During treatment delivery, radiation source 1010 may be rotatable using a gantry around a patient, or the patient may be rotated (as in some proton radiotherapy solutions) to emit radiation beam 1020 at various beam orientations or angles relative to the patient. For example, five equally-spaced beam angles 1030A-E (also labelled "A," "B," "C," "D" and "E") may be selected using an AI engine configured to perform treatment delivery data estimation. In practice, any suitable number of beam and/or table or chair angles 1030 (e.g., five, seven, etc.) may be selected. At each beam angle, radiation beam 1020 is associated with fluence plane 1040 (also known as an intersection plane) situated outside the patient envelope along a beam axis extending from radiation source 1010 to treatment volume 1060. As shown in FIG. 10, fluence plane 1040 is generally at a known distance from the isocenter.

In addition to beam angles 1030A-E, fluence parameters of radiation beam 1020 are required for treatment delivery. The term "fluence parameters" may refer generally to characteristics of radiation beam 1020, such as its intensity profile as represented using fluence maps (e.g., 1050A-E for corresponding beam angles 1030A-E). Each fluence map (e.g., 1050A) represents the intensity of radiation beam 1020 at each point on fluence plane 1040 at a particular beam angle (e.g., 1030A). Treatment delivery may then be performed according to fluence maps 1050A-E, such as using IMRT, etc. The radiation dose deposited according to fluence maps 1050A-E should, as much as possible, correspond to the treatment plan generated according to examples of the present disclosure.

Computer System

Figure 11:
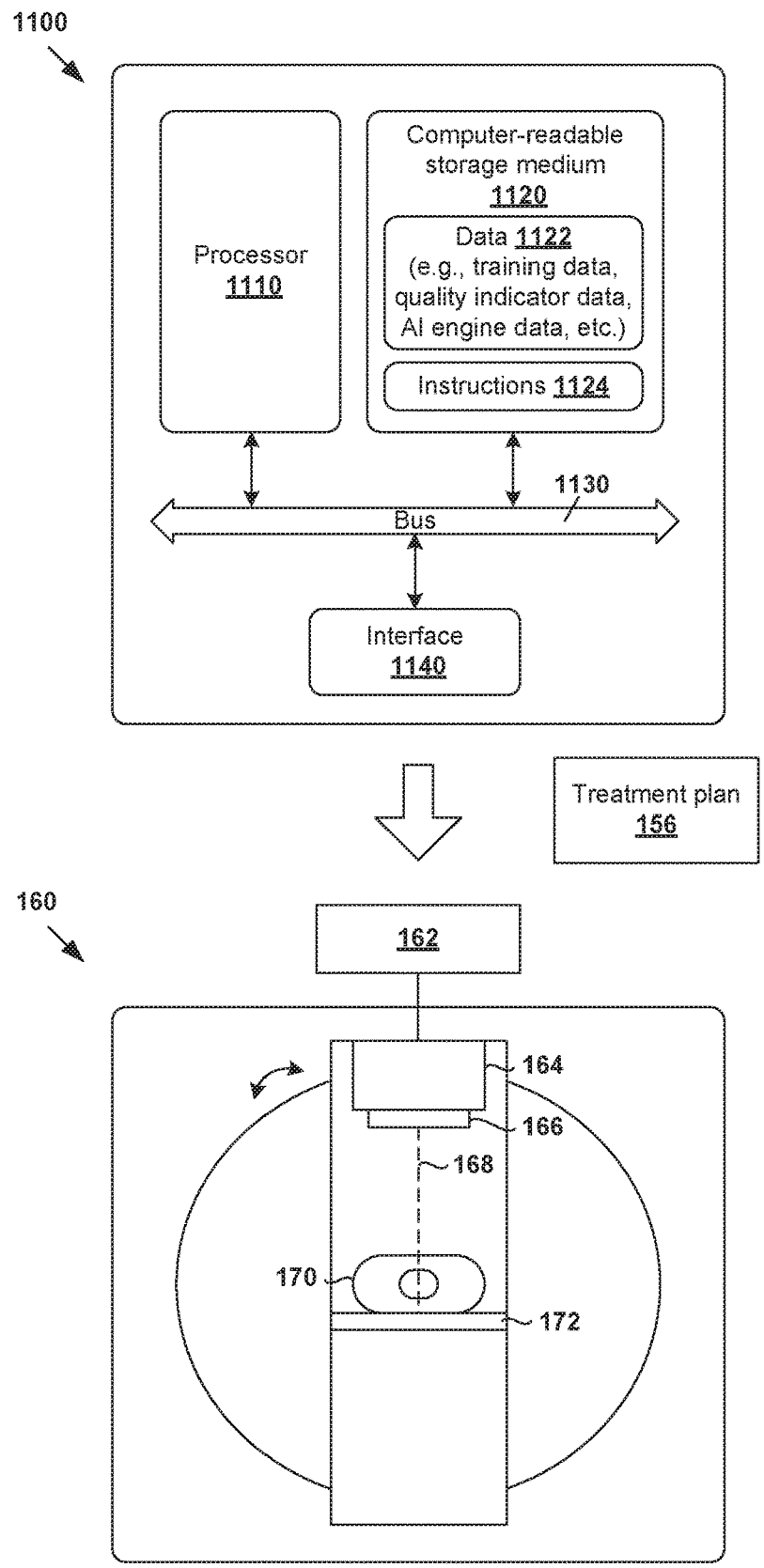
FIG. 11 is a schematic diagram of an example computer system to perform quality-aware continuous learning for radiotherapy treatment planning.

The above examples can be implemented by hardware, software or firmware or a combination thereof. FIG. 11 is a schematic diagram of example computer system 1100 for quality-aware continuous learning for radiotherapy treatment planning. In this example, computer system 1105 (also known as a treatment planning system) may include processor 1110, computer-readable storage medium 1120, interface 1140 to interface with radiotherapy treatment delivery system 160, and bus 1130 that facilitates communication among these illustrated components and other components.

Processor 1110 is to perform processes described herein with reference to FIG. 1 to FIG. 9. Computer-readable storage medium 1120 may store any suitable information 1122, such as information relating to training data, AI engines, weight data, input data, output data, etc. Computer-readable storage medium 1120 may further store computer-readable instructions 1124 which, in response to execution by processor 1110, cause processor 1110 to perform processes described herein. Treatment may be delivered according to treatment plan 156 using treatment planning system 160 explained using FIG. 1, the description of which will not be repeated here for brevity.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to perform quality-aware continuous learning for radiotherapy treatment planning, wherein the method comprises:

obtaining an artificial intelligence (AI) engine that is trained to perform a radiotherapy treatment planning task;

based on input data associated with a patient, performing the radiotherapy treatment planning task using the AI engine to generate output data associated with the patient;

obtaining modified output data that includes one or more modifications made by a treatment planner to the output data;

performing quality evaluation of the modified output data based on at least one of (a) first quality indicator data associated with the modified output data, and (b) second quality indicator data associated with the treatment planner;

accepting the modified output data based on the quality evaluation; and generating a modified AI engine by re-training the AI engine based on the modified output data.

2. The method of claim 1, wherein performing quality evaluation comprises:
determining the first quality indicator data as statistical parameter data by applying one or more statistical models on the modified output data.

3. The method of claim 1, wherein performing quality evaluation comprises:
identifying the treatment planner from multiple treatment planners; and
determining the second quality indicator data as a credibility score assigned to the treatment planner.

4. The method of claim 1, wherein generating the modified AI engine comprises:
assigning a case weight to the modified output data based on at least one of (a) the first quality indicator data, and (b) the second quality indicator data.

5. The method of claim 1, wherein the method further comprises:
obtaining planner-generated output data that is generated by multiple treatment planners based on multiple treatment planning cases;
based on the planner-generated output data, determining consensus truth data associated with the multiple treatment planning cases; and
based on a comparison between the planner-generated output data and the consensus truth data, assigning the second quality indicator data as a credibility score to each of the multiple treatment planners.

6. The method of claim 1, wherein the method further comprises:
performing the radiotherapy treatment planning task by using the AI engine to generate multiple sets of output data based on respective multiple techniques associated with the radiotherapy treatment planning task; and
obtaining the modified output data from a particular set of output data that is selected by the treatment planner from the multiple sets, wherein the particular set of output data is generated based on one of the multiple techniques.

7. The method of claim 1, wherein the method further comprises one of the following:
selecting, from multiple treatment planners, a panel of experts to review the modified output data based on multiple credibility scores assigned to the respective multiple treatment planners;
selecting, from multiple treatment planners, a particular treatment planner to a particular radiotherapy treatment planning task based on a particular credibility score assigned to the particular treatment planner; and
determining, for a particular treatment planner, a reward based on a particular credibility score assigned to the particular treatment planner.

8. The method of claim 1, wherein performing the radiotherapy treatment planning task comprises:
performing automatic segmentation using the AI engine to generate an output structure data based on an input image data associated with a particular patient;
performing dose prediction using the AI engine to generate an output dose data based on the input image data and an input structure data associated with the particular patient; and
performing treatment delivery data prediction using the AI engine to generate treatment delivery data based on an input dose data associated with the particular patient.

9. A non-transitory computer-readable storage medium that includes a set of instructions which, in response to execution by a processor of a computer system, cause the processor to perform a method of quality-aware continuous learning for radiotherapy treatment planning, wherein the method comprises:
obtaining an artificial intelligence (AI) engine that is trained to perform a radiotherapy treatment planning task;
based on input data associated with a patient, performing the radiotherapy treatment planning task using the AI engine to generate output data associated with the patient;
obtaining modified output data that includes one or more modifications made by a treatment planner to the output data;
performing quality evaluation of the modified output data based on (a) first quality indicator data associated with the modified output data, and (b) second quality indicator data associated with the treatment planner;
accepting the modified output data based on the quality evaluation; and
generating a modified AI engine by re-training the AI engine based on the modified output data.

10. The non-transitory computer-readable storage medium of claim 9, wherein performing quality evaluation comprises:
determining the first quality indicator data as statistical parameter data by applying one or more statistical models on the modified output data.

11. The non-transitory computer-readable storage medium of claim 9, wherein performing quality evaluation comprises:
identifying the treatment planner from multiple treatment planners; and
determining the second quality indicator data as a credibility score assigned to the treatment planner.

12. The non-transitory computer-readable storage medium of claim 9, wherein generating the modified AI engine comprises:
assigning a case weight to the modified output data based on at least one of (a) the first quality indicator data, and (b) the second quality indicator data.

13. The non-transitory computer-readable storage medium of claim 9, wherein the method further comprises:
obtaining planner-generated output data that is generated by multiple treatment planners based on multiple treatment planning cases;
based on the planner-generated output data, determining consensus truth data associated with the multiple treatment planning cases; and
based on a comparison between the planner-generated output data and the consensus truth data, assigning the second quality indicator data as a credibility score to each of the multiple treatment planners.

14. The non-transitory computer-readable storage medium of claim 9, wherein the method further comprises:
performing the radiotherapy treatment planning task by using the AI engine to generate multiple sets of output data based on respective multiple techniques associated with the radiotherapy treatment planning task; and
obtaining the modified output data from a particular set of output data that is selected by the treatment planner from the multiple sets, wherein the particular set of output data is generated based on one of the multiple techniques.

15. The non-transitory computer-readable storage medium of claim 9, wherein the method further comprises one of the following:
- selecting, from multiple treatment planners, a panel of experts to review the modified output data based on multiple credibility scores assigned to the respective multiple treatment planners;
- selecting, from multiple treatment planners, a particular treatment planner to a particular radiotherapy treatment planning task based on a particular credibility score assigned to the particular treatment planner; and
- determining, for a particular treatment planner, a reward based on a particular credibility score assigned to the particular treatment planner.

16. The non-transitory computer-readable storage medium of claim 9, wherein performing the radiotherapy treatment planning task comprises:
- performing automatic segmentation using the AI engine to generate an output structure data based on an input image data associated with a particular patient;
- performing dose prediction using the AI engine to generate an output dose data based on the input image data and an input structure data associated with the particular patient; and
- performing treatment delivery data prediction using the AI engine to generate treatment delivery data based on an input dose data associated with the particular patient.

17. A computer system configured to perform quality-aware continuous learning for radiotherapy treatment planning, wherein the computer system comprises: a processor and a non-transitory computer-readable medium having stored thereon instructions that, when executed by the processor, cause the processor to:
- obtain an artificial intelligence (AI) engine that is trained to perform a radiotherapy treatment planning task;
- based on input data associated with a patient, perform the radiotherapy treatment planning task using the AI engine to generate output data associated with the patient;
- obtain modified output data that includes one or more modifications made by a treatment planner to the output data;
- perform quality evaluation of the modified output data based on (a) first quality indicator data associated with the modified output data, and (b) second quality indicator data associated with the treatment planner;
- accept the modified output data based on the quality evaluation; and
- generate a modified AI engine by re-training the AI engine based on the modified output data.

18. The computer system of claim 17, wherein the instructions comprise instructions for performing the quality evaluation that, when executed by the processor, cause the processor to:
- determine the first quality indicator data as statistical parameter data by applying one or more statistical models on the modified output data.

19. The computer system of claim 17, wherein the instructions comprise instructions for performing the quality evaluation that, when executed by the processor, cause the processor to:
- identify the treatment planner from multiple treatment planners; and
- determine the second quality indicator data as a credibility score assigned to the treatment planner.

20. The computer system of claim 17, wherein the instructions comprise instructions for generating the modified AI engine that when executed by the processor, cause the processor to:
- assign a case weight to the modified output data based on at least one of (a) the first quality indicator data, and (b) the second quality indicator data.

21. The computer system of claim 17, wherein the instructions further cause the processor to:
- obtain planner-generated output data that is generated by multiple treatment planners based on multiple treatment planning cases;
- based on the planner-generated output data, determine consensus truth data associated with the multiple treatment planning cases; and
- based on a comparison between the planner-generated output data and the consensus truth data, assign the second quality indicator data as a credibility score to each of the multiple treatment planners.

22. The computer system of claim 17, wherein the instructions further cause the processor to:
- perform the radiotherapy treatment planning task by using the AI engine to generate multiple sets of output data based on respective multiple techniques associated with the radiotherapy treatment planning task; and
- obtain the modified output data from a particular set of output data that is selected by the treatment planner from the multiple sets, wherein the particular set of output data is generated based on one of the multiple techniques.

23. The computer system of claim 17, wherein the instructions further cause the processor to perform one of the following:
- select, from multiple treatment planners, a panel of experts to review the modified output data based on multiple credibility scores assigned to the respective multiple treatment planners;
- select, from multiple treatment planners, a particular treatment planner to a particular radiotherapy treatment planning task based on a particular credibility score assigned to the particular treatment planner; and
- determine, for a particular treatment planner, a reward based on a particular credibility score assigned to the particular treatment planner.

24. The computer system of claim 17, wherein the instructions comprise instructions for performing the radiotherapy treatment planning task that, when executed by the processor, cause the processor to:
- perform automatic segmentation using the AI engine to generate an output structure data based on an input image data associated with a particular patient;
- perform dose prediction using the AI engine to generate an output dose data based on the input image data and an input structure data associated with the particular patient; and
- perform treatment delivery data prediction using the AI engine to generate treatment delivery data based on an input dose data associated with the particular patient.

* * * * *